United States Patent [19]

Farmer et al.

[11] Patent Number: 5,458,142
[45] Date of Patent: Oct. 17, 1995

[54] DEVICE FOR MONITORING A MAGNETIC FIELD EMANATING FROM AN ORGANISM

[76] Inventors: Edward J. Farmer; Diane J. Hovey, both of 1611 20th St., Sacramento, Calif. 95814

[21] Appl. No.: 33,900

[22] Filed: Mar. 19, 1993

[51] Int. Cl.⁶ ........................................................ A61B 5/00
[52] U.S. Cl. ........................ 128/653.1; 128/905; 324/260
[58] Field of Search ................................. 128/653.1, 905; 600/9, 10, 11; 324/244, 260

[56] References Cited

U.S. PATENT DOCUMENTS

| | | | |
|---|---|---|---|
| 3,721,230 | 3/1973 | Ziernicki . | |
| 3,727,604 | 4/1973 | Sidwell et al. . | |
| 3,951,134 | 4/1976 | Malech . | |
| 4,134,395 | 1/1979 | Davis . | |
| 4,557,271 | 12/1985 | Stoller et al. | 128/734 |
| 4,602,639 | 7/1986 | Hoogendoorn et al. | 128/639 |
| 4,625,732 | 12/1986 | Kasa et al. | 128/670 |
| 4,688,580 | 8/1987 | Ko et al. | 128/734 |
| 4,690,149 | 9/1987 | Ko | 128/653 |
| 4,697,599 | 10/1987 | Woodley et al. . | |
| 4,719,425 | 1/1988 | Ettinger | 324/316 |
| 4,864,282 | 9/1989 | Toeg | 340/573 |
| 4,930,516 | 6/1990 | Alfano et al. | 128/665 |
| 4,940,058 | 7/1990 | Taff et al. | 128/653.1 |
| 4,951,674 | 8/1990 | Zanakis et al. | 128/653 R |
| 4,961,428 | 10/1990 | Nikias et al. | 128/699 |
| 5,003,979 | 2/1991 | Merickel et al. . | |
| 5,020,538 | 6/1991 | Morgan et al. | 128/653.1 |
| 5,092,835 | 3/1992 | Schurig et al. | 600/9 |
| 5,152,288 | 10/1992 | Hoenig et al. | 128/653.1 |
| 5,183,456 | 2/1993 | Liboff et al. | 600/9 |
| 5,261,405 | 11/1993 | Fossel | 128/653.2 |
| 5,307,807 | 5/1994 | Valdes Sosa et al. | 128/653.1 |

*Primary Examiner*—Ruth S. Smith
*Attorney, Agent, or Firm*—Bernhard Kreten

[57] ABSTRACT

A diagnostic and therapeutic instrument for use in the treatment of living organisms is provided including a sensor for detecting magnetic fields emanating from the living organism. The sensor is located proximate to the organism and is formed from a ferromagnetic core surrounded by a multi-turn fine wire coil. The sensor is coupled to signal processing which amplifies a signal from the sensor and filters out portions of the signal which represent background magnetic fields emanating from other sources. The signal from the sensor is utilizable to detect abnormalities in the field emanating from the organism indicative of the organism's well-being. The signal can also be utilized to excite a magnetic field radiator which outputs a field complementary to the field emanating from the organism.

7 Claims, 5 Drawing Sheets

DEVICE FOR MONITORING A MAGNETIC FIELD EMANATING FROM AN ORGANISM

FIELD OF THE INVENTION

The present invention relates to the systems, methods, and apparatus by which the electromagnetic emissions of a living organism may be monitored. Specifically, the present invention relates to the systems, methods, and means whereby the physical state and emotional state of an organism and the changes in the physical and emotional state of the organism can be monitored.

It also provides a means of altering the physical state and emotional state of an organism by the introduction of specific compensatory and corrective electromagnetic patterns associated with the physical and emotional condition of the organism.

BACKGROUND OF THE INVENTION

The concept of an energy field around a living organism that reflects its physical condition is a central concept in Aurvedic medicine dating back 5,000 years. The idea has appeared multiple times in different cultures and at different times in history. It provides the foundation for healing practices in Tibetan, Chinese, and Hawaiian medicine. The energy field is seen as having multiple layers ranging from a greater density near the body to a rarefied layer encircling the body and extending a greater distance therefrom. In all of the aforementioned philosophies, the layer closest to the body is believed to reflect its physical condition while those extending outward represent emotional and spiritual conditions. In Sanskrit, the word describing the energy field is "prana," in Chinese it is called "chi" and Hawaiian it is called "aka." It has also been called the etheric field or aura. In all philosophies, illness is believed to be the result of a lack of or imbalance in the energy field around the body and can be observed by examining the field. Healing and regeneration can only take place when the energy field is balanced and strong.

The validity and acceptability of these ancient philosophies are of present interest and are being tested with traditional western medicine. Dr. Deepak Chopra, M.D., FACS, former chief of staff of New England Memorial Hospital in Stoneham, Mass. has devoted considerable attention to combining traditional western medicine with Aurvadic philosophy. Dr. Chopra has chosen to use the term "Ayurveda" (instead of the more common "Aurvada") because in his judgement this spelling more properly reflects the Sanskrit roots of this philosophy. In his books, which include *Perfect Health, Creating Health,* and *Quantum Healing,* he provides many case histories to support his concept of Ayurvedic medicine. He characterizes the Ayurvedic field with an analogy with quantum mechanics which he expresses thus:

"In Ayurveda, the physical body is the gateway to what I call the "quantum mechanical human body." Physics informs us that the basic fabric of nature lies at the quantum level, far beyond atoms and molecules. A quantum, defined as the basic unit of matter or energy, is from 10,000,000 to 100,000,000 times smaller than the smallest atom. At this level, matter and energy become interchangeable. All quanta are made of invisible vibrations—ghosts of energy—waiting to take physical form. Ayurveda says that the same is true of the human body—it first takes form as intense but invisible vibrations, called quantum fluctuations, before it proceeds to coalesce into impulses of energy and particles of matter.

The quantum mechanical body is the underlying basis for everything we are: thoughts, emotions, proteins, cells, organs-any visible or invisible part of ourselves. At the quantum level, your body is sending out all kinds of invisible signals, waiting for you to pick them up."

Dr. Delores Krieger, RN researched the energy fields described in these ancient philosophies and through rigorous controlled experiments documented the healing that resulted from manipulating these energy fields. She continued this research and taught the technique she named "Therapeutic Touch" throughout her 20 year tenure as professor of neurophysiology at the New York University School of Nursing until her recent retirement. She now teaches and speaks on the subject at medical and nursing schools across the country.

During Dr. Krieger's research she met and continued to work with one of the few individuals who profess to be able to actually see this energy field, Dora Van Gelder Kunz. As part of Dr. Krieger's establishment of an experimentally documented baseline that would establish credibility with mainstream medicine, both women participated in a study arranged by Elmer Green, Ph.D., Director of Research at the Menniger Foundation. The study was conducted during a Council Grove Conference during which a patient was brought in from another state along with his physician and a complete set of lab reports. Each woman was allowed to examine the patient over a 15 minute period, but were not permitted to talk with the person. At the end of their examination each woman presented her findings to a panel of five physicians and the patient's physician. Dora Kunz's diagnosis was rated at 100 percent while Dr. Krieger received a rating of 80 percent.

A Therapeutic Touch practitioner that is unable to see the etheric field around the body assesses the patient's condition by moving both hands over the energy field surrounding the patient's body. The perceived differences in the field indicate injury or disease in the underlying body structure. The assessment has been described by many experienced practitioners as the most difficult part of the process because it is frequently very difficult to feel the differences in the field of a very ill patient, or a child.

The present invention has demonstrated a high degree of correlation with the impressions of practitioners trained and experienced in therapeutic touch. It serves to augment therapeutic touch as a diagnostic tool. It also serves as a training aid in teaching therapeutic touch.

Tests with the apparatus have also established predictable electromagnetic field variations resulting from changes in mental activity level. For example, the waveform emitted by the subject becomes significantly more complex when responding to a command question requiring the subject to generate a specific type of visual image. The increase in complexity occurs in the absence of speech and when speech is required, precedes verbalization of the response and decays rapidly when the verbal response is complete.

Tests involving stress, including situations in which the subject attempts to provide false answers to questions, produce more complex and higher amplitude responses than situations in which the subject experiences less stress.

Others have addressed the concept of diagnosis through external measurements by monitoring skin potential using various techniques. These techniques use contacting sensors and monitor direct current flow on the surface of the body, and hence do not monitor fields about the body or emissions therefrom. They demonstrate the state of the art in non-invasive monitoring and diagnostic techniques.

Dr. Robert O. Becker, MD, who was head of the Surgical Department at the U.S. Veteran's Administration Hospital in Syracuse, N.Y., did considerable work with what he called "micropotentials" around injuries and their effect on healing. He also studied the effects of low frequency radio emissions on humans.

Dr. Becker described his research thusly:

"My research began with experiments on regeneration, the ability of some animals, notably the salamander to grow perfect replacements for parts of the body that have been destroyed. These studies led to the discovery of a hitherto unknown aspect of animal life—the existence of electrical currents in parts of the nervous system. This breakthrough in turn led to a better understanding of bone fracture healing, new possibilities for cancer research, and hope of human regeneration—even of the heart and spinal cord—in the not to distant future. Finally, a knowledge of life's electrical dimension has yielded fundamental insights into pain, healing, growth, consciousness, the nature of life itself, and the dangers of our electromagnetic technology.

I believe these discoveries presage a revolution in biology and medicine. One day they may enable the physician to control and stimulate healing at will."

His research focused on the bio-electrical "current of injury," a change in potential at the site of injury, that initiated the healing process in salamanders and frogs with the hope the information could be applied to his surgical patients. This research brought him together with Dr. Charles Bachman from the Syracuse University Physics Department. Together they demonstrated that a semiconducting DC current flows through the body of the frog utilizing the motor nerves for positive direction and sensory nerves for negative. Likewise the current flowing through the salamander's brain followed a similar pattern and anaesthesia could be induced by regulating the current. A similar test on human subjects also demonstrated a variation in back-to-front current varied with changes in consciousness just as in salamanders. It was strongest during heightened physical or mental activity, it declined during rest, and it reversed direction in both normal sleep and anaesthesia.

From this research a small electrical generator connected to silver mesh "cloth" was developed to speed tissue and bone regeneration.

On a National Institute of Health grant requested by the Army Surgeon General's office, Becker demonstrated the DC flow through acupuncture points and their meridians and confirmed they followed the same pattern established in his work with amphibians. "Each point was positive compared to its environs, and each one had a field surrounding it, with its own characteristic shape . . . It was obvious . . . that at least a major part of the acupuncture charts has an objective basis in reality."

Dr. Becker and Dr. David Cohen of MIT's Francis Bitter National Magnet Laboratory used the superconducting quantum interferometric device (SQUID) to measure the human head. Dr. Becker summarized the laboratories' work thus, "They found two kinds of magnetic fields. Quickly reversing AC fields produced by the back and forth ion currents in nerve and muscle. They're strongest in the heart, since its cells contract in synchronal. The SQUID has also confirmed the existence of the DC perineural system, which, especially in the brain, produces steady DC magnetic fields one billionth the strength of the earth's field of about one-half gauss."

Dr. Becker's work resulted in U.S. Pat. No. 4,557,271 for a "Method and Apparatus for Detecting Body Illness, Dysfunction, Disease and/or Pathology." Dr. Becker based his patent on a method for "non-invasively measuring bioelectric potentials at selected dermal (skin) points on the body of man to detect existing or impending illness, dysfunction, disease and/or pathology." His sensing apparatus used "D.C. potential sensing, microgrid electrodes forming voltage input means to the digital neurometer instrumentation. For most measurement purposes the microgrid electrodes are interfaced with bilateral dermal sites on the fingers and toes of the subject. Generally, the microgrid sensing electrodes contact the terminal phalanx of the fingers and toes of the subject. The bilateral microgrid electrodes and bilateral ground electrodes are connected to a high input impedance linear amplifier which converts the very low D.C. biopotentials sensed by the microgrid electrodes and ground/electrodes into low impedance higher voltage signals." He goes on to describe computer processing of the signals.

Dr. Becker fixated on skin surface potentials and the analysis thereof. Many medical instruments are based on potentials measured on the surface of the skin, the electrocardiogram (EKG) being a notable example.

In 1975, Drs. Samuel Williamson, Lloyd Daufman, and Douglas Brenner of NYU succeeded in measuring the head's field without a shielded enclosure, even amid the electromagnetic noise of downtown Manhattan. More important, they found that the magnetoencephalogram (MEG)—a recording of changes in the brain's field analogous to the EEG—is often a more accurate reflection of mental activity than the EEG.

The present invention is focused on the concept of the Aurvedic field itself as opposed to skin surface potentials that may or may not be related directly to it. A radiating field that can interact with another human sensor would, in classical physics, be explained in terms of thermal radiation, an electrostatic field, an electromagnetic field, or some new force.

Thermal analysis has been used as a medical diagnostic technique for years. It is well understood that higher temperatures exist near injuries than in surrounding tissue. Thermal imaging can be conducted by contacting thermal sensors or by infrared sensitive cameras. While this can be an effective diagnostic tool in some situations it has not exhibited a very broad range of application.

Based on the work of Becker and others, an electrostatic field does exist between locations on the body. Differences in potential exist between locations on a single body and as Leon Ernst Eeman demonstrated in the 1920s in England, it is possible to create potential paths that can form circuits involving multiple persons. These are essentially D.C. circuits. Eeman received a U.K. Patent around 1922 for a bio-circuit device. The bio-circuit is based on his hypothesis that humans radiate energy, and this energy radiates more powerfully or accumulates more readily at specific areas of the body. These locations can be linked together to create a circuit that enhances recuperative processes and produces a flow of energy. He called this energy the "energy of life" although the characteristics he described for it more closely position it with Becker's micropotentials. Eeman's bio-circuit consists of two copper mesh pads connected together with a length of wire. Each pad also has a copper handle connected to it by a wire. The patient assumes a reclining position with one pad under his head and the other under his lower back. He then crosses his legs at the ankles and grasps one handle in each hand. The circuit balanced the energy potential across the body and enhanced healing. Eeman used this device in his London healing practice from 1922 until shortly before his death in 1958.

Not only are the signals involved in the operation of the present invention of very low intensity but they are effectively masked by the much higher levels of the fields created by electric power systems (60 Hz. in the United States). The applicants' research indicates the emissions of interest for diagnostic and therapeutic purposes are in the range of 0.1 to 30 Hz. Because of the low frequencies and their closeness to 60 Hz their presence has been effectively masked to less persistent investigators.

The present invention is the only technique that has been shown to correlate with the judgments of persons trained in therapeutic touch. It is the only technique that provides all measurements on the basis of electromagnetic emissions. It does not require contact with the subject of the examination. It does not rely on potential differences between locations on the skin nor on where or how such measurements are made.

The present apparatus has effectively dealt with the 60 Hz. masking problem by active filtering to reduce the composite signal to one in which the 60 Hz. noise is no longer the dominant component and then using digital filtering techniques, in a computer analysis program, to remove the remaining 60 Hz. components as well as decompose the composite time-domain signal into its frequency domain constituents.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| U.S. PAT. NO. | ISSUE DATE | INVENTOR |
| --- | --- | --- |
| 3,721,230 | March 20, 1973 | Ziernicki |
| 3,727,604 | April 17, 1973 | Sidwell, et al. |
| 3,951,134 | April 20, 1976 | Malech |
| 4,134,395 | January 16, 1979 | Davis |
| 4,557,271 | December 10, 1985 | Stoller, et al. |
| 4,602,639 | July 29, 1986 | Hoogendoorn, et al. |
| 4,625,732 | December 2, 1986 | Kasa, et al. |
| 4,688,580 | August 25, 1987 | Ko, et al. |
| 4,690,149 | September 1, 1987 | Ko |
| 4,697,599 | October 6, 1987 | Woodley, et al. |
| 4,719,425 | January 12, 1988 | Ettinger |
| 4,864,282 | September 5, 1989 | Toeg |
| 4,961,428 | October 9, 1990 | Nikias, et al. |
| 4,951,674 | August 28, 1990 | Zanakis, et al. |
| 5,003,979 | April 2, 1991 | McRickel, et al |
| 5,092,835 | March 3, 1992 | Schurig, et al. |

Zanakis et al were awarded U.S. Pat. No. 4,951,674 for a Biomagnetic Analytical System Using Fiber-Optic Magnetic Sensors. Zanakis' system is primarily oriented toward mapping the points of emission of low level radiation from the brain or other tissue. Zanakis includes a "magnetic shield" surrounding his sensor array so that, "sensors in the array are magnetically shielded from each other to prevent magnetic interaction therebetween as well as from magnetic fields extraneous to the region of interest, thereby obviating the need for a shielded room to conduct studies on biomagnetic activity." This allows his apparatus to concentrate on the extremely low level emissions, which he describes as having an intensity of "about one picotesla (1 pT=$10^{-12}$ T)" from within the brain itself and to determine the location within the brain that is the source of the emissions He further notes that, "The magnetic field emanating from the brain has a strength much below that emitted by the heart. Hence monitoring of brain magnetic activity presents formidable difficulties."

Zanakis further teaches, "The characteristics of biomagnetic activity that are measurable are the strength of the field, the frequency domain and the nature of the field pattern outside of the body." It should be noted that by, ". . . outside the body" Zanakis clearly means, "and within the magnetic shield."

Zanakis also teaches, "In biomagnetic analysis, three types of magnetic sensors are known to have adequate sensitivity and discrimination against ambient noise for this purpose. The first is the induction coil. But because of Nyquist noise associated with the resistance of the windings and its loss of sensitivity at frequencies below a few Herz, the induction coil is rarely used in MEG studies."

The present invention is differentiated from the Zanakis system is several ways.

The signals for which the present invention is monitoring have been observed to be on the order of $10^{-6}$ Gauss ($10^{-10}$ Tesla) at reasonable distance (e.g., 1 to 6 inches) from human subjects. This is two orders of magnitude greater than the signals for which Zanakas' apparatus is optimized.

While Zanakas apparently appreciated that electromagnetic emissions other than those in which he was interested occurred (e.g., his concern about the magnitude of the field produced by the heart), he failed to attach significance to them, either in whole or in part. He characterized emissions from the heart in terms of the difficulty they created relative to his stated purpose of monitoring emissions from the brain. Zanakas failed to realize that eliminating, for example, heart rate induced components in this measurements was well within the state of the signal processing art.

Further, the design of Zanakas' apparatus is focused on eliminating, ". . . magnetic fields extraneous to the region of interest . . . " The present invention makes use of the organism's field in its totality as well as changes detected in that field while moving the sensor above the surface of the organism. While Zanakas' approach was probably productive for accomplishing a magnetic emission map of the brain (or "other tissue") it actually works to eliminate the influence of all other naturally occurring sources of emission within the organism. In that respect, the present invention and that of Zanakas are completely different in their approach and in their intended use.

Zanakas attributes Nyquist noise to his problems with induction coil type sensors. Much of the advantage he attributes to SQUID type sensors is specifically directed toward lowering the Nyquist noise by reducing resistance and decreasing temperature. In fact, in the frequency range of interest in the context of this invention, and at normal temperatures of operation, and with proper design of the induction coil sensor, Nyquist noise in the sensor is at least three orders of magnitude (60 dB) below the lowest signal levels required for effective operation of the present invention. Consequently, the applicants believe that Zanakas attributed the emissions that are the subject of this invention to be Nyquist noise. This would indicate Zanakas did not understand the nature of the emissions with which this invention is concerned and that the purpose of his apparatus was, in fact, much more narrowly focused than his disclosure of it would indicate.

While Zanakas mentions the spectra of the emissions can be measured he does not indicate what significance should or can be attached to them. The present invention's operation is based in large part on interpreting the spectra of the emissions.

SUMMARY OF THE INVENTION

Monitoring Device

A method, system, and apparatus are described for monitoring the physical and emotional state, and the changes in the physical and emotional state, of a living organism by means of the electromagnetic emissions of the organism.

A sensor designed for monitoring extremely low level, low frequency electromagnetic signals is used to detect emissions from the organism under test. Since emissions of this type attenuate rapidly with increasing distance, and since the emissions associated with injuries vary with location on the organism relative to the injury, the sensor is mounted in such as way to permit positioning about the organism.

The output of the sensor is connected to an instrumentation amplifier by means of two-conductor shielded cable.

The instrumentation amplifier incorporates a differential input, high gain, high impedance, low noise and a guard output. The differential input reduces common mode noise from the sensor and interconnecting cable. The high gain minimizes attenuation of the signal resulting from loading of the sensor and interconnecting wiring. The low noise minimizes the noise contributed to the amplifier's output by the internal circuits of the amplifier, and the guard output is used to drive the shield of the interconnecting wiring to lower signal loss from the two conductors to the shield.

The output of the instrumentation amplifier is connected to a series of low pass filters. These filters attenuate signals with frequencies above those of primary interest, particularly power line frequencies (e.g., 60 Hz or 50 Hz.).

The output of the low pass filters is passed to an analog to digital converter. This converter has sufficient dynamic range to resolve all amplitudes of interest and sufficient bandwidth to pass all frequencies of interest.

The output of the analog to digital converter is read by a computer program for further processing. This additional processing includes display and measurement of the waveform and measurement and display of the frequency components of the waveform.

The data pertaining to the frequency components taken separately and in conjunction with their relative amplitudes can be used to infer the physical and emotional condition of the organism under test. The changes in the waveform, its constituent frequencies and their amplitudes can be used to infer changes in the emotional and physical state of the organism.

Therapeutic Device

A method, system, and apparatus are described for modifying the physical and emotional state of a living organism by means of the electromagnetic emissions.

A radiator designed for producing low level, low frequency electromagnetic signals is used to provide emissions complementary to the emissions from the organism under test. Since emissions of this type attenuate rapidly with increasing distance, and since the emissions associated with injuries vary with location on the organism relative to the injury, the sensor is mounted in such a way as to permit positioning about the organism.

The radiator is connected to an amplifier by means of two-conductor shielded cable.

The amplifier is used to generate signals complementary to the signals characteristic of physical or emotional irregularities radiated from the organism.

The amplifier is driven by a function generator that can produce a series of selectable frequencies with selectable amplitudes, said frequencies and amplitudes having been selected for their therapeutic value.

The amplifier may also be driven by a phase-adjusted and filtered signal derived from the sensor described above. In this configuration the specific frequency components indicative of a physical or emotional difficulty are isolated by filtering, modified in phase and amplitude, and then fed to the radiator. This combination of sensor, processor, radiator forms a closed loop (feedback) system providing self-regulation of the therapeutic process.

OBJECTS OF THE INVENTION

Accordingly, it is a primary object of the present invention to provide a method of monitoring the electromagnetic emissions of living organisms.

Another object of the invention is to provide a method of monitoring a living organism that does not require physical contact with the organism or the injection of chemicals or substances of any kind.

Another object of the invention is to provide a method of monitoring a living organism that does not subject the organism to externally generated signals of any kind (e.g., x-rays, ultrasound, magnetic fields, heat).

Another object of the invention is to provide an indication of the changes in the physical condition of an organism.

Another object of the invention is to provide an indication of the changes in the emotional condition of an organism.

Another object is to provide a means of diagnosing the physical condition of an organism.

Another object is to provide biofeedback for assisting in the teaching of therapeutic touch.

Another object is to provide a means of detecting changes in the emotional state of an organism due to physical stress.

Another object is to provide a means of detecting changes in the emotional state of an organism due to emotional stress.

A second primary object of the present invention is to provide an instrumentality for providing therapeutic electromagnetic signals.

Another object is to provide an electromagnetic field with the proper frequency components of the proper amplitude to counterbalance the signals characteristic of specific emotional or physical problems.

Another object is to provide an electromagnetic field with the proper frequency components of the proper amplitude and phase to counterbalance signals indicative of specific emotional or physical conditions as monitored at the same time by the sensor system described above, thus providing a closed-loop self-regulating therapeutic system.

Viewed from a first vantage point, it is an object of the present invention to provide a device for monitoring a magnetic field emanating from an organism, comprising in combination: sensor means proximate the organism; a signal emanating from the sensor means; an amplifier receiving the signal from the sensor means and amplifying the signal; a filter receiving the signal and filtering out components of the signal which are not indicative of the organism's magnetic field; and an output means coupled to the filter.

Viewed from a second vantage point it is a further object of the present invention to provide a magnetic field sensor for sensing magnetic fields originating from an organism, including a coil of conductive material having a first end and a second end, the material wrapped a plurality of times about a core, the core comprised of a material having a high permeability to magnetic flux; and an output device coupled to the coil and sensitive to a potential difference between the first end and the second end, the potential difference comprising a signal.

Viewed from a third vantage point it is a further object of the present invention to provide a method for harnessing magnetic fields surrounding an organism including the steps of forming an organism interface proximate the organism by placing a wire winding onto a ferromagnetic loop and adjacent the organism, and amplifying a signal associated with the loop reflective of the organism effecting the wire and loop whereby the magnetic fields surrounding the organism can be used for diagnosis or treatment of the organism.

These and other objects will be made manifest when considering the following detailed specification when taken in conjunction with the appended drawing figures.

DESCRIPTION OF THE PREFERRED EMBODIMENTS

Figure 1:
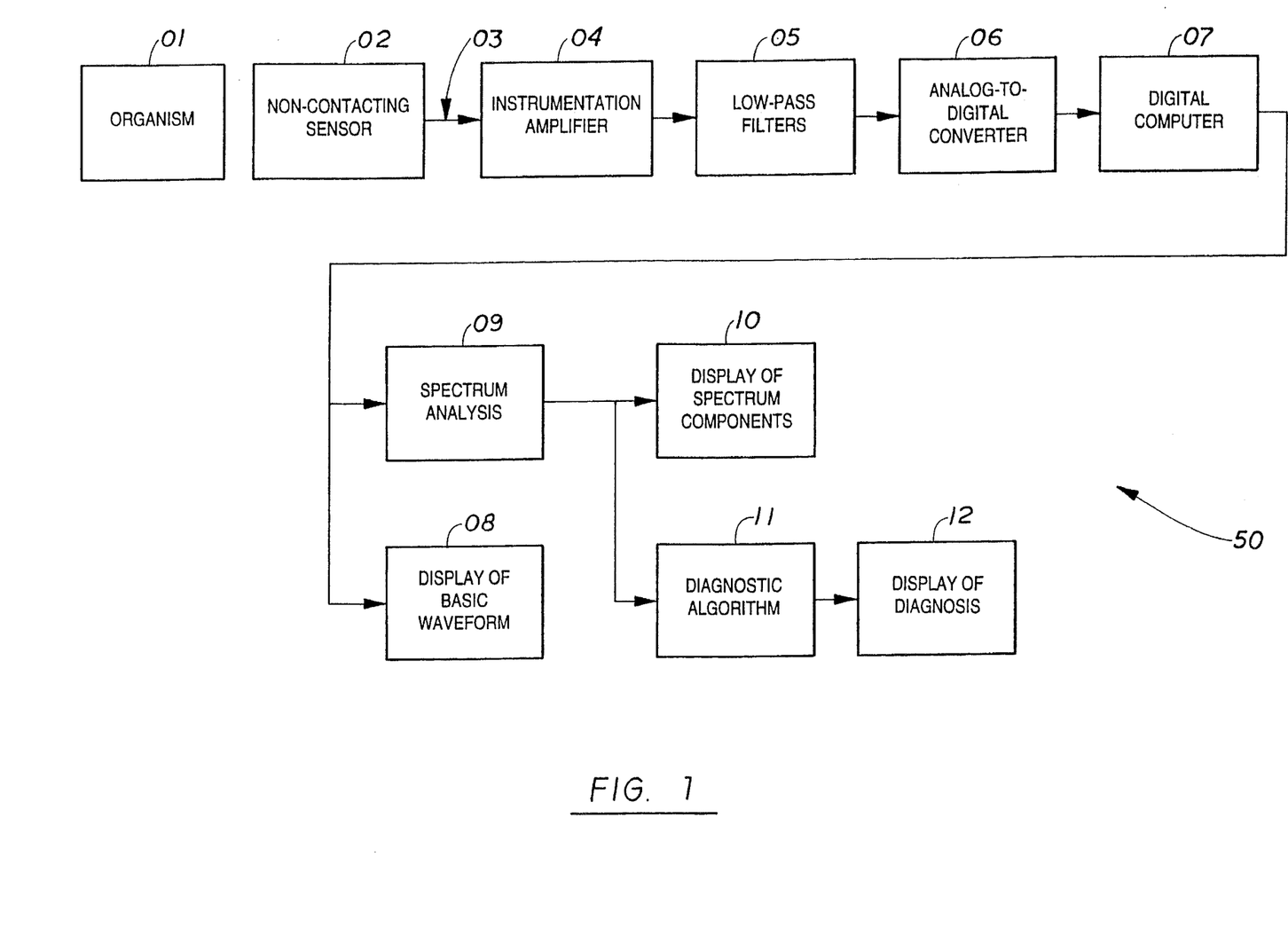
FIG. 1 is a schematic drawing of the device of this invention when used to sense a magnetic field from the organism and diagnose any illness based on characteristics of a signal from the sensor.
Figure 2:
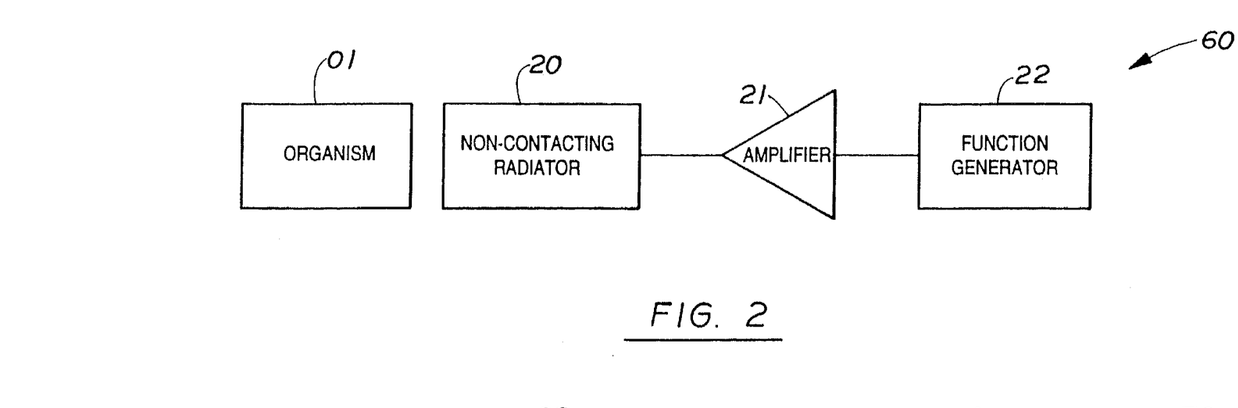
FIG. 2 is a schematic drawing of an alternative embodiment of this invention where the signal is used to drive a magnetic field radiator for treatment of the organism.

Referring now to the drawing figures wherein like numerals represent like parts throughout, numeral 50 of FIG. 1 represents an emission monitoring means and 60 of FIG. 2 represents a therapeutic radiating means.

In essence, the emission monitoring means 50, includes the following basic components. A sensor 02 is located in the proximity of the organism, or part thereof, that is to be monitored. This sensor 02 may be in contact with the organism 01 or may not be in contact with the organism 01 as desired however it is anticipated that the ability to monitor without contact will be the preferred embodiment. The sensor 02 is connected by wiring 03 to instrumentation amplifier 04. The amplified signal is connected to filters 05 and then converted from analog to digital form by analog-to-digital converter 06. The converted signal is then processed in a computer 07 where the resulting waveform is displayed 08 for use by the operator. Simultaneously, the signal is analyzed using digital signal processing techniques 09 to extract its frequency spectrum and the magnitude of each frequency component. The resulting spectrum is displayed 10 for use by the operator and also provided as an input for diagnostic algorithms 11. The results of the diagnostic analysis is displayed 12 for use by the operator.

More specifically, the sensor 02 is located in the proximity of the organism 01 or part thereof from which emissions are to be monitored.

The sensor 02 is a device that can convert magnetic fields to electrical signals. Please see FIG. 4. Such a device can be fabricated by selecting a ferromagnetic core material, such as steel, iron, or ferrite, and winding a large number of turns of wire 102 onto it. A spool 101 is used to contain and support the wire 102. A suitable sensor can be fabricated by use of a 3,250 inch diameter by 10-inch long steel rod 100. Approximately 20,000 turns of #29 AWG wire 102 is wound around it using a plastic spool 101 to support the wire. There are other devices that can function as a suitable sensor. A fluxgate device is one such example.

Figure 5:
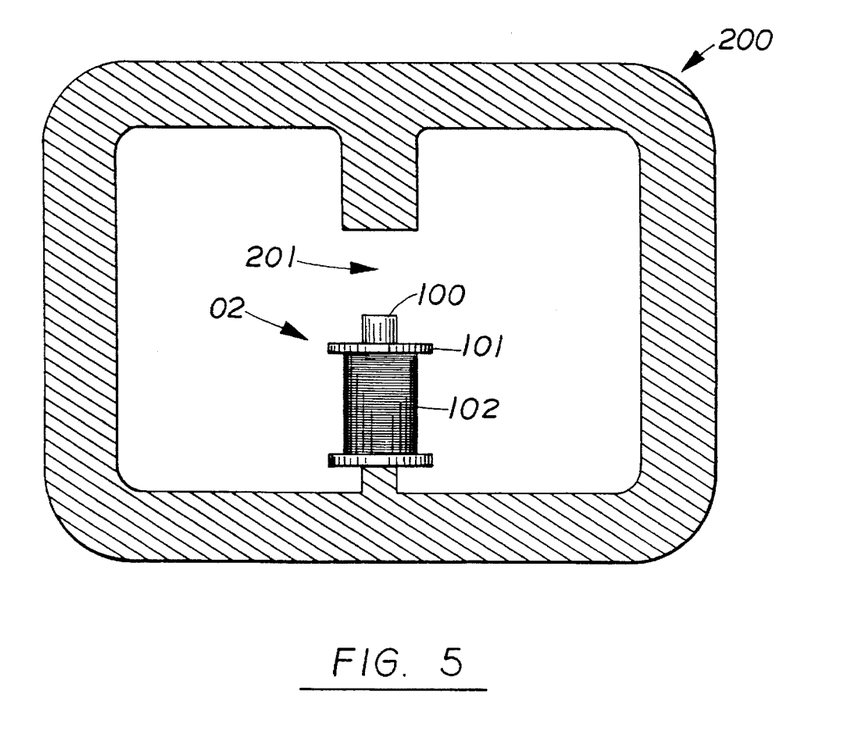
FIG. 5 is a front view of the sensor of this invention with a magnetic circuit included therein.

Since the strength of emissions decrease rapidly with distance, the emissions near the sensor 02 will be dominant. The response of the sensor 02 to emissions from a specific position on the organism 01 can be enhanced by providing an apparatus that causes the magnetic path in the vicinity of the area of interest to be optimized. This is done by providing a magnetic circuit enhancing means 200 as shown in FIG. 5. This magnetic circuit enhancing means can be made of any ferromagnetic material, such as iron or steel. Materials of higher permeability (such as ferrite) are preferred. The sensitivity will be highest for emissions that occur in the gap 201.

The output of the sensor 02 is connected to the amplifier 04 by means of a two-conductor shielded cable 03. Please see FIG. 1. One of the conductors is connected to the positive input and the other to the negative input of the instrumentation amplifier 04. The "guard" output of the instrumentation amplifier 04 is connected to the shield of this cable to provide shielding from extraneous radiation, to enhance the common mode rejection of the amplifier-sensor combination, and to preserve the high input impedance of the instrumentation amplifier.

The output of the instrumentation amplifier 04 is connected to low pass filters 05. Since the sensor and amplifier respond to all electromagnetic fields they will exhibit a very large response to the usually substantial fields associated with normal electrical wiring. This produces very large amplitude signals compared to those of interest in the monitoring of organisms. Typically, the fields at the frequency of the electrical power lines will be several orders of magnitude larger than those emitted from the organism under test 01. In the preferred embodiment these power system generated signals are removed by low pass filtering using at least three stages of active filters 05. These filters provide nominal gain (2 in the preferred embodiment) and high rejection above their design cutoff frequency. The design cut-off frequency would ideally be about 30 Hz. Using a lower cut-off frequency provides more attenuation at the power line frequency but does also attenuate some of the higher frequencies of interest. In the preferred embodiment a cutoff frequency of 10 Hz was used. This allowed adequate rejection of the 60 Hz power line signal with three stages of filtering 05. Once the amplitude of the 60 Hz noise is reduced below the peak level of the signal of interest it can be digitized without wasting a portion of the dynamic range of the analog to digital converter 06.

The resulting signal is converted from analog form to digital form by the analog to digital converter means 06. This device should have sufficient dynamic range to resolve the largest and smallest signals of interest. In the preferred embodiment a resolution of 16 bits was used providing a range of 65,536 to 1, or 96.33 dB.

The output of the analog-to-digital converter 06 is read into a digital computer 07. This computer provides for display of these very low frequency, slowly changing signals 08 and also provides an analysis means 09 from which the frequency and amplitude of the constituent components of the measured waveform can be identified and displayed on the display means 10. The preferred technique for spectrum analysis is the "Fast Fourier Transform" which is well reported in the literature. A new transform is performed and the display 10 updated each time a new reading is available.

The output of the spectrum analysis means 09 is also processed by a diagnostic algorithm processing means 11. This processing amounts to correlating the frequency spectrum and the amplitudes of the components thereof with cataloged patterns associated with certain conditions of interest. This correlation is done using conventional pattern recognition techniques.

The results of said diagnostic means is provided for use by the operator on the display means 12. This output is typically a written explanation of the condition and the logic behind the conclusion.

Therapeutic Implementation

Figure 3:
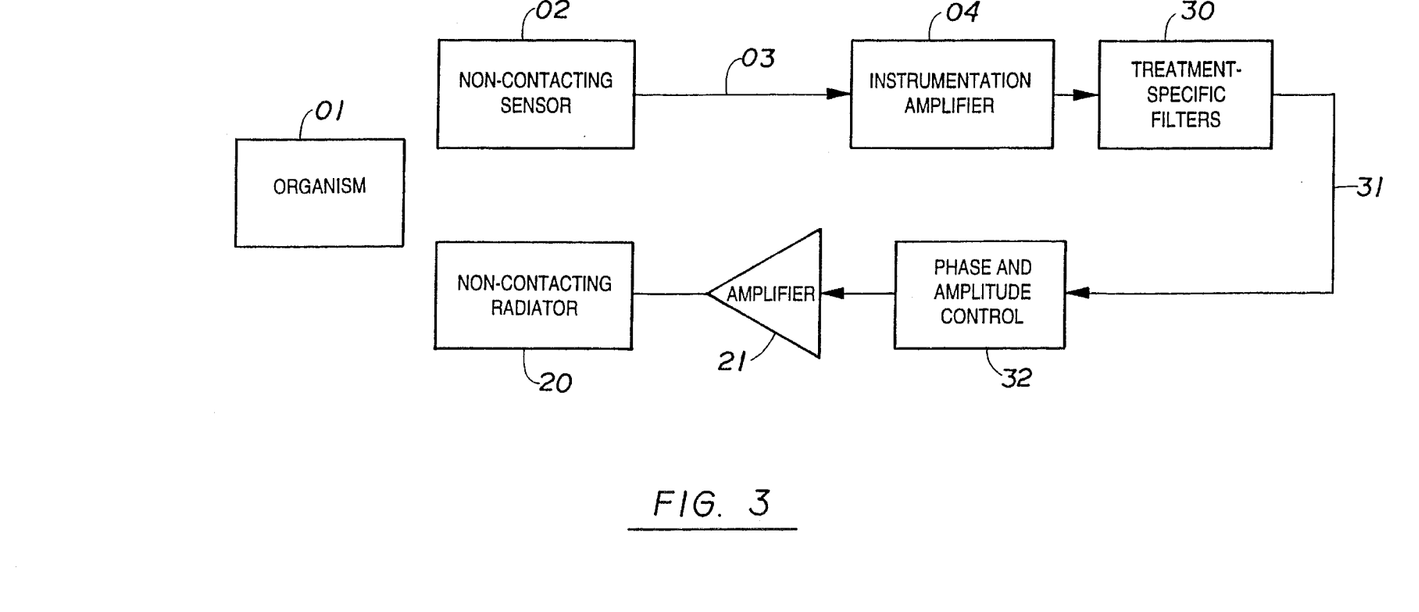
FIG. 3 is a schematic drawing of an alternative embodiment of this invention which utilizes the signal generated from the device of FIG. 1 to drive the device of FIG. 2.

Referring now to FIGS. 2 and 3 wherein like numerals represent like parts throughout, numeral 60 represents a therapeutic radiating means.

In essence, the radiating means 60, includes the following basic components. A radiating device 20 is located in the proximity of the organism, or part thereof, that is to be treated. This radiator may be in contact with the organism or may not be in contact with the organism as desired however it is anticipated that the ability to do a treatment without contact will be the preferred embodiment. The radiator is driven by a power amplifier 21 which receives its signal from a function generator 22. This function generator 22 is capable of generating waveforms with specific frequency content as selected by the operator.

More specifically, the radiator 20 is located in the proximity of the organism 01 or part thereof from which emissions are to be monitored. It is identical in construction to the monitoring sensor 02 except that it is wound with fewer turns of wire 102. The smaller number of turns is possible because the quantity of magnetic flux emitted by the radiator 20 can be readily controlled by practical amplifiers 21 of relatively high gain. Approximately 100 turns of #22 AWG wire are sufficient.

The function generator 22 is used to generate a signal with the proper frequency and amplitude content. The frequencies are selected on the basis of the condition to be treated. The amplitudes are selected on the basis of the condition to be treated and in consideration of the proximity of the sensor 02 and the radiator 20 to the area of the organism that is to receive the treatment.

Suitable function generators 22 are available from Hewlett Packard Corporation (e.g., their Model HP 3245A and Model HP 3314A) but are more readily implemented by using digital signal processing software on a computer. Constants representing the desired frequencies and amplitudes are provided to an inverse Fourier Transform algorithm which then generates the time domain equivalent signal. The output from the digital signal processing algorithm is converted to analog form by a digital-to-analog converter which is then used to drive the amplifier means 21.

Alternatively, FIG. 3 indicates that a radiator means 20 can be used in conjunction with a sensor means 02 to provide automatic feedback-stabilized corrective signals. The output from the sensor 02 is transmitted to an amplifier 04 by means of interconnecting wiring 03. The specific frequency components indicative of the problem requiring therapy are extracted by treatment specific filter means 30. The output from said filter means 30 are modified in phase and amplitude by control means 32. The processed signal is then provided as the input to the amplifier 21 and then to the radiator means 20.

Figure 4:
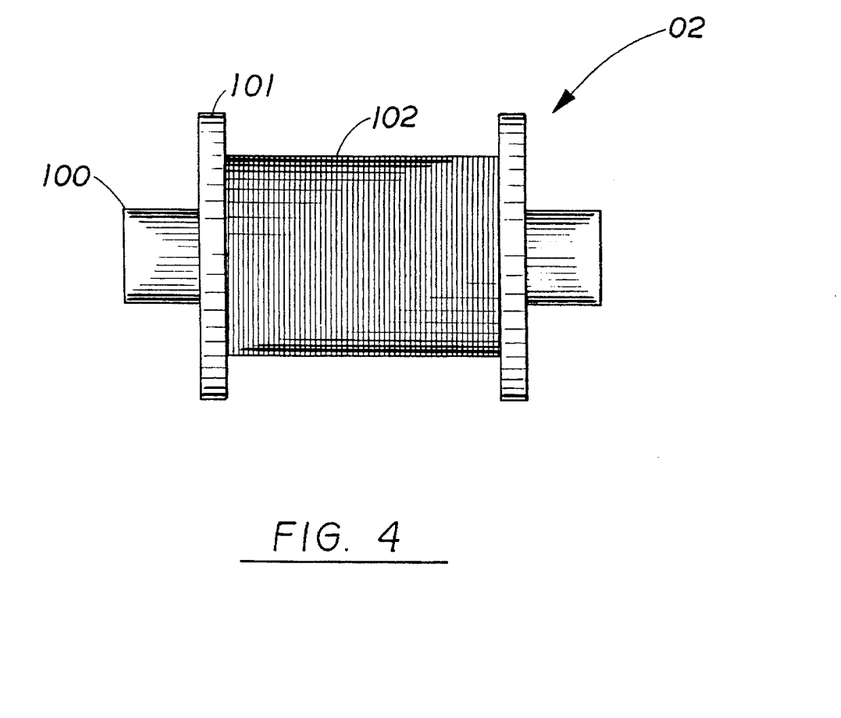
FIG. 4 is a front view of the sensor of this invention.
Figure 6:
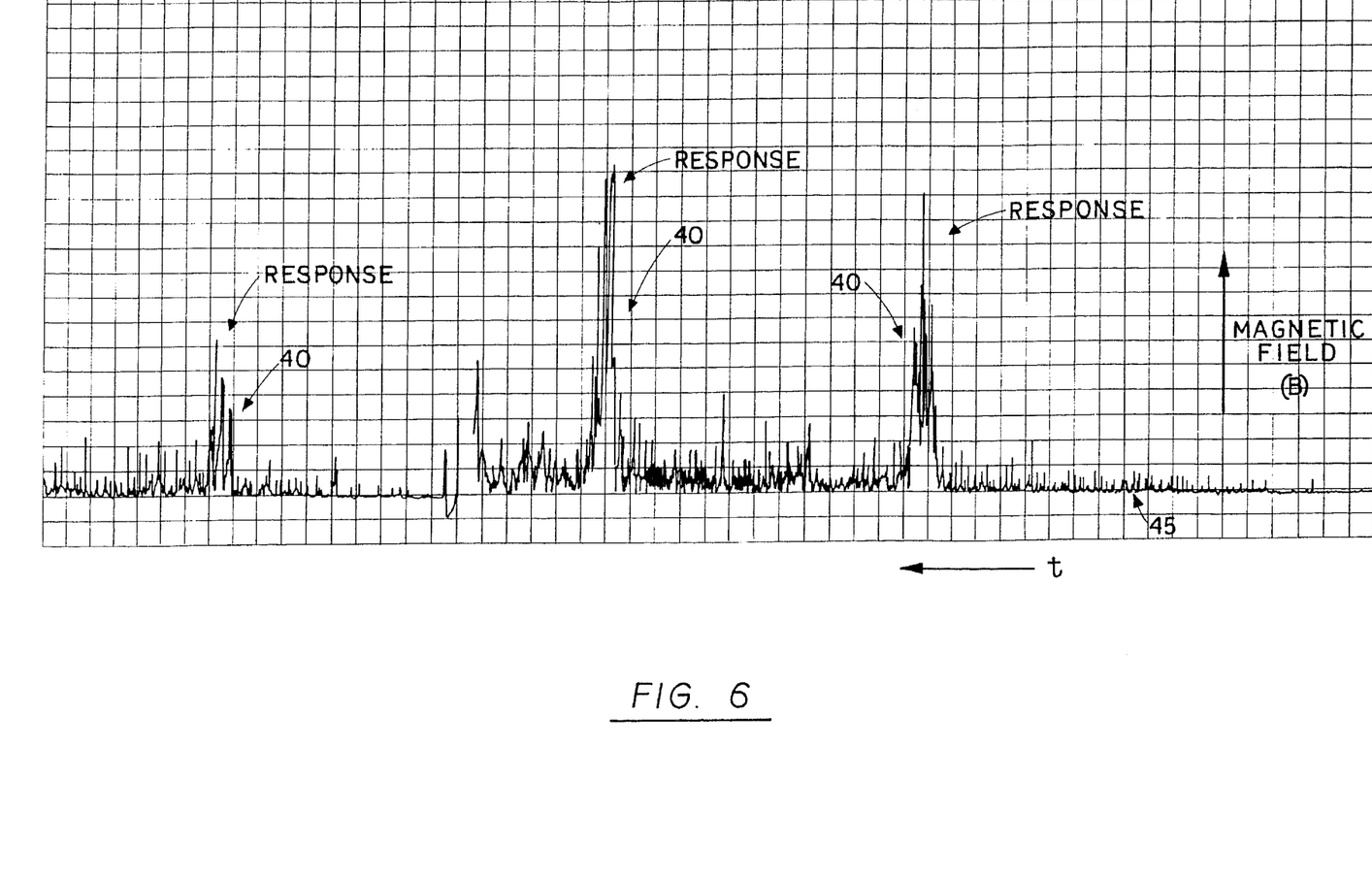
FIG. 6 is a graphic representation of the signal produced by the sensor of this invention indicating changes in magnetic field of a person corresponding to responses to questions and other stimuli.

Referring in detail to FIGS. 4 and 6, details of one use of this invention is described. When students are being trained in the practice of therapeutic touch, it is often difficult for the student to develop a personal magnetic field of sufficient intensity to be useful in monitoring or treating a patient. Once the student has mastered the ability to generate a sufficient field, the student can have difficulty identifying when a patient is emitting an abnormal field and what malady is associated with the abnormality.

The sensor 02, shown in FIG. 4, can be utilized to assist the student in enhancing his/her personal magnetic field. A magnetic field radiator 20 can be used to give the student practice in recognizing magnetic fields of the type emitted by a patient under various conditions. Specifically, the student wishing to hone his/her personal magnetic field, especially that existing between the student's hands, places his/her hands near opposite ends of the core 100 of the sensor 02.

The magnetic field produced by the student is then monitored by the sensor 02 in conjunction with a display output of some sort. One form of display is a graph of magnetic field vs. time as is shown in FIG. 6. When an increased magnetic field is detected the student has an opportunity to recall which "actions" caused the increase in the magnetic field. With practice, the student will learn to control his/her ability to generate such a magnetic field.

FIG. 6 reveals output from the sensor 02 when the sensor 02 is oriented between the hands of a skilled therapeutic touch practitioner. When questions were asked of the practitioner, a spike 40 of activity would result. These spikes 40 are indicative of responses (both verbal and nonverbal) to the questions posed. The FIG. 6 data indicates that increased mental activity is one source of increased magnetic field emission.

In other tests, changes in magnetic field were detected when the sensor 02 was passed adjacent locations on a patient where injuries had occurred. Not only are magnitudes of the field emanating from the patient of interest, but also frequency components existing in the signal 03 captured by the sensor provide an indication of the condition of the patient. While many of the connections between magnetic field characteristics and physical condition have yet to be verified by repeated experimentation, the sensor 02 effectively quantifies the properties of this field such that such research can take place in an objectively quantifiable manner.

Figure 7:
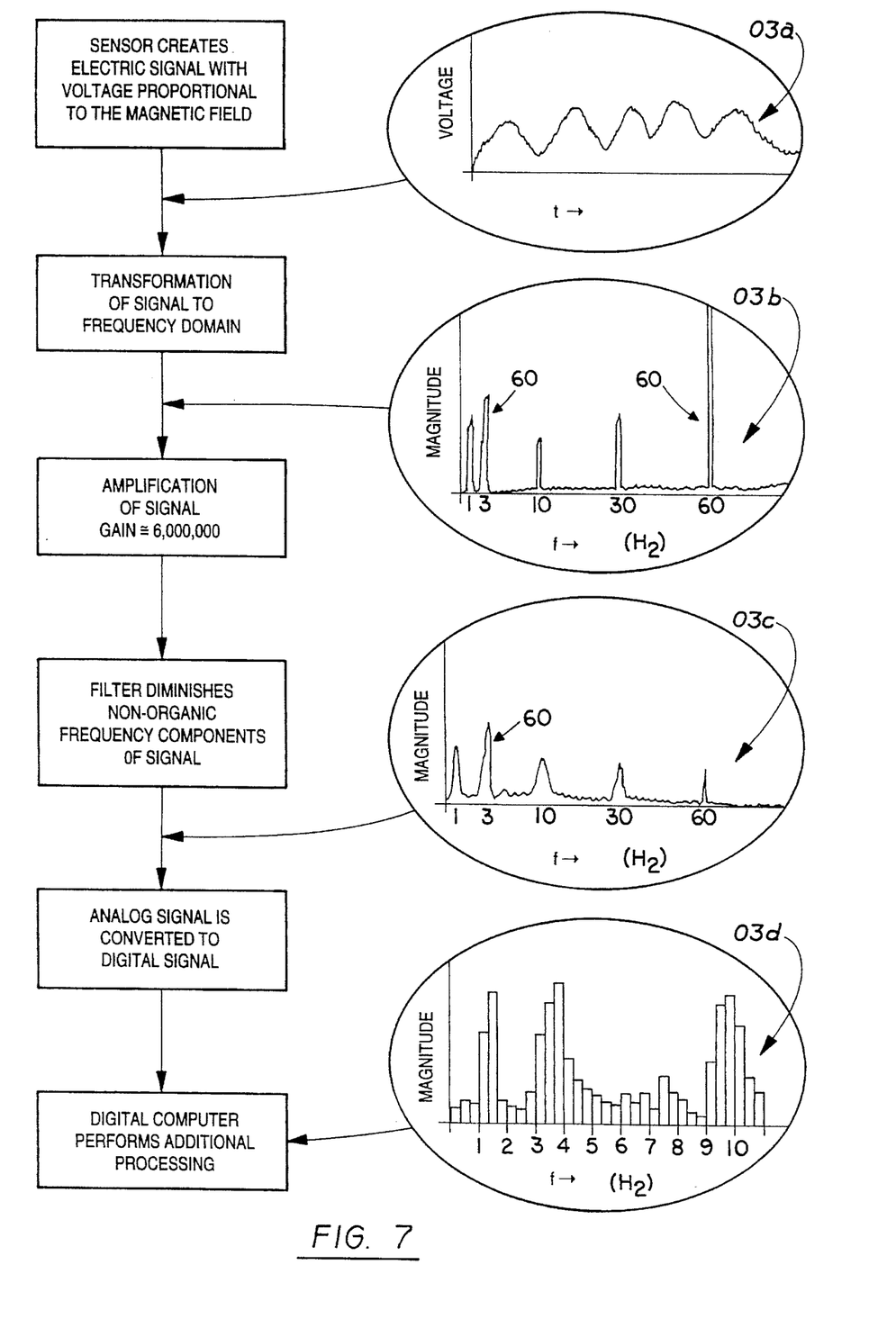
FIG. 7 is a flow chart revealing steps in the signal processing of the signal produced by the sensor with waveforms corresponding to different portions of the processing shown graphically.

In use and operation, and as described in FIG. 7, the sensor 02 generates the signal 03 such that it can be utilized for diagnosis and / or treatment in the following manner. Initially, the sensor 02 (with or without the magnetic circuit 200) detects the magnetic field proximate to the sensor 02 and creates a signal 03*a* having a voltage proportional to the magnetic field intensity encountered by the sensor 02. This signal is typically characterized by having a very low amplitude and exhibiting a number of different frequency components riding thereon. The signal 45 shown in FIG. 6 is exemplary of one form that signal could take.

To isolate these frequencies, the signal 03*a* is transformed into the frequency domain using methods known in the art as Fourier analysis. This transformation results in a signal 03*b* having spikes 70. These spikes 70 are distinct from the spikes 40 shown in FIG. 6 in that the spikes 70 represent a high magnitude of energy at the specific frequency represented. Note, for instance, that a spike 70 occurs at approximately 60 Hz. This spike 70 indicates that various electric power sources in the region having a frequency of 60 Hz have generated magnetic fields detectable by the sensor 02. Other spikes 70 represent activity associated with the magnetic field emanating from the patient.

The signals 03*a*, 03*b* are extremely low in magnitude as compared to the contribution normally evident at 60 Hz. Accordingly, an amplifier is used to provide the signal 03*b* with sufficient gain that in can be thoroughly analyzed. With a sensor 02 such as that described above with a 3,250-inch diameter 10-inch long ferromagnetic core and 20,000 turns of wire 102 about the core 100 an amplifier-filter chain with a gain of approximately 6,000,000 (720 dB) has been effectively utilized.

High frequency components of the signal 03*b* are usually quite large and not indicative of the magnetic field emanating from the patient. Thus, it is often desirable to filter out frequencies above approximately 30 Hz to facilitate closer scrutiny of the more indicative lower frequency components. Typically, this filtration can be done through a low pass filter 05 (shown in FIG. 1) of a type common in the signal processing art. This filtration typically results in a signal 03*c*. Note that the signal 03*c* has a dramatically reduced magnitude at the 60 Hz frequency.

The signal 03*c* is of a form which lends itself readily to conversion into a digital form through an analog-to-digital (A/D) converter (not shown). The A/D converter allows the signal 03*d* to be inputted into a digital processor such as a digital computer for further processing of the signal 03*d*. Specifically, details of the low frequency components of the signal 03*d* can be enhanced for analysis. Also, any remaining frequency component at the 60 Hz level can be removed.

Once the signal 03*d* has been purified to more exactly indicate magnetic field details representative of the patient's condition, the signal 03*d* can be utilized for diagnosis or for treatment. One form of treatment involves inverting the signal, converting the signal 03*d* back into an analog signal, amplifying the signal and utilizing the signal to drive a non-contacting radiator 20 such as that represented schematically in FIG. 3.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A device for monitoring a magnetic field emanating from an organism, comprising in combination:

sensor means to sense a magnetic field adapted to be positioned proximate to the organism;

said sensor means including means to generate a signal representative of the magnetic field and emanating from said sensor means;

an amplifier receiving said signal from said sensor means and amplifying said signal;

a filter receiving said signal, said filter including means to filter out components of said signal which are not indicative of the organism's magnetic field;

an output means to output said signal from said filter, said output means coupled to said filter;

wherein said filter includes means to further filter out components of said signal having a frequency similar to that exhibited by non-organic magnetic field sources; whereby portions of the signal from other non-organic magnetic field sources are filtered out of said signal;

wherein said device includes means to transform said signal from a time domain into a frequency domain and said output means includes means to interpret said signal to determine the prevalence of different frequency components within said signal, wherein said device includes an analog-to-digital converter interposed between said sensor means and said output means, said converter including means to receive as input said signal in analog form and means to output said signal in a digital form, said digital form compatible with a digital computer such that the signal can be inputted into a digital computer for processing; and wherein said sensor means is a coil of wire wrapped around a ferromagnetic core, the wire having opposite ends, and means to monitor said ends for the voltage potential generated therebetween.

2. The device of claim 1 wherein a digital computer is interposed between said converter and said output, said digital computer including means to still further filter said signal and means to enhance said signal.

3. A device for monitoring a magnetic field emanating from an organism, comprising in combination:

sensor means to sense a magnetic field adapted to be positioned proximate to the organism;

said sensor means including means to generate a signal representative of the magnetic field and emanating from said sensor means;

an amplifier receiving said signal from said sensor means and amplifying said signal:

a filter receiving said signal, said filter including means to filter out components of said signal which are not indicative of the organism's magnetic... field; and an output means to output said signal from said filter, said output means coupled to said filter, wherein said sensor means includes a coil of electrically conductive wire, said coil of wire having at least one-thousands (1,000) turns therein wrapped around a ferromagnetic core, said wire including opposite ends and said sensor means including means to measure a voltage between said opposite ends.

4. The device of claim 3 wherein said amplifier has a gain of one-hundred thousand (100,000).

5. The device of claim 3 wherein said sensor means includes a magnetic circuit formed from ferromagnetic material arranged in a loop attached to said ferromagnetic core at one end of said ferromagnetic core, passing about an exterior of said coil of wire and coming to a location adjacent to an opposite end of said core, said circuit spaced from said opposite end of said core by a gap, said gap having a sufficient width to allow portions of the organism to be located within said gap.

6. The device of claim 3 wherein an analog-to-digital converter is interposed between said filter and said output means, said analog-to-digital converter includes means to convert said signal from analog to digital, and wherein said output means includes a digital computer, said digital computer receiving said signal from said analog-to-digital converter in digital form, said computer including means to convert said signal from a time based domain to a frequency based domain.

7. The device of claim 6 wherein said digital computer includes means to filter out portions of said signal having frequencies greater than thirty (30) Hertz.

* * * * *